(12) United States Patent
Auner et al.

(10) Patent No.: US 7,837,944 B2
(45) Date of Patent: Nov. 23, 2010

(54) DEVICE FOR SEPARATING AND CONCENTRATING MICROFLUIDIC PARTICLES

(75) Inventors: Gregory W. Auner, Livonia, MI (US); Chung Chu Chen, Novi, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 12/265,291

(22) Filed: Nov. 5, 2008

(65) Prior Publication Data

US 2009/0173700 A1    Jul. 9, 2009

Related U.S. Application Data

(63) Continuation of application No. PCT/US2007/011060, filed on May 7, 2007.

(60) Provisional application No. 60/797,998, filed on May 5, 2006.

(51) Int. Cl.
*B01L 99/00* (2010.01)
(52) U.S. Cl. .......................... 422/101; 422/99
(58) Field of Classification Search ............... 436/174, 436/177, 180; 422/100, 101; 55/462
See application file for complete search history.

(56) References Cited

U.S. PATENT DOCUMENTS 1,603,878 A    10/1926   Smith
2,532,332 A *  12/1950   Rowand ............... 55/444
3,591,000 A    7/1971    Humphreys
4,153,541 A    5/1979    Rumpf et al.
4,159,942 A    7/1979    Greer et al.
4,990,740 A    2/1991    Meyer
5,609,771 A    3/1997    Pelmulder
5,641,622 A    6/1997    Lake et al.
5,652,148 A    7/1997    Doshi et al.

(Continued)

FOREIGN PATENT DOCUMENTS

WO    WO 98/58725    12/1998

OTHER PUBLICATIONS

A. Marziali, T. D. Willis, R. W. Davis, "An Arrayable Flow-Through Microcentrifuge for High-Throughput Instrumentation," Proc. Natl. Acad. Sci. USA, vol. 96, pp. 61-66, 1999.

(Continued)

*Primary Examiner*—Yelena G Gakh
*Assistant Examiner*—Christopher A Hixson
(74) *Attorney, Agent, or Firm*—Brinks Hofer Gilson & Lione

(57) ABSTRACT

A flow unit for microfluidic particles separation and concentration is disclosed. The unit comprises a nozzle segment, a turn segment, and a diffuser segment. The nozzle segment is defined by a first member and a second member, and has an opening through which fluid and microfluidic particles enter. The nozzle segment has a narrowing portion at which the first and second members narrow from the opening to increase momentum of the fluid therethrough. The turn segment is defined by the first member flaring outwardly downstream from the narrowing portion to change flow direction of the fluid consistent with the first member. The diffuser segment is defined by the second member extending past the turn segment to facilitate separation of the microfluidic particles from the fluid due to the inability to follow the fluid flow.

13 Claims, 5 Drawing Sheets

U.S. PATENT DOCUMENTS

| | | |
|---|---|---|
| 5,660,798 A | 8/1997 | Doshi et al. |
| 5,663,051 A | 9/1997 | Vlasselaer |
| 5,715,946 A | 2/1998 | Reichenbach |
| 2004/0232052 A1 | 11/2004 | Call et al. |

OTHER PUBLICATIONS

J. C. Giddings, "Field-Flow Fraction—Analysis of Macromolecular, Colloidal, and Particulate Materials," Science, vol. 260, pp. 1456-1465, 1993.

T. Chianea, N. E. Assidjo, P. J. P. Cardot, "Sedimentation Field—Flow Fractionation : Emergence of a New Cell Separation Methodology," Talanta, vol. 51, pp. 835-847, 2000.

V. Yue, R. Kowal, L. Neargarder, L. Bond, A. Muetterties, R. Parsons, "Miniature Field—Flow Fractionation System for Analysis of Blood Cells," Clin. Chem., vol. 40, pp. 1810-1814, 1994.

H. M. Eppich, et al., "Pulsed Electrical Fields for Selection of Hematopoietic Cells and Depletion of Tumor Cell Contaminants," Nature Biotechnol., vol. 18, pp. 882-887, 2000.

International Search Report—PCT/US2007/011060 (mailed Apr. 4, 2008).

* cited by examiner

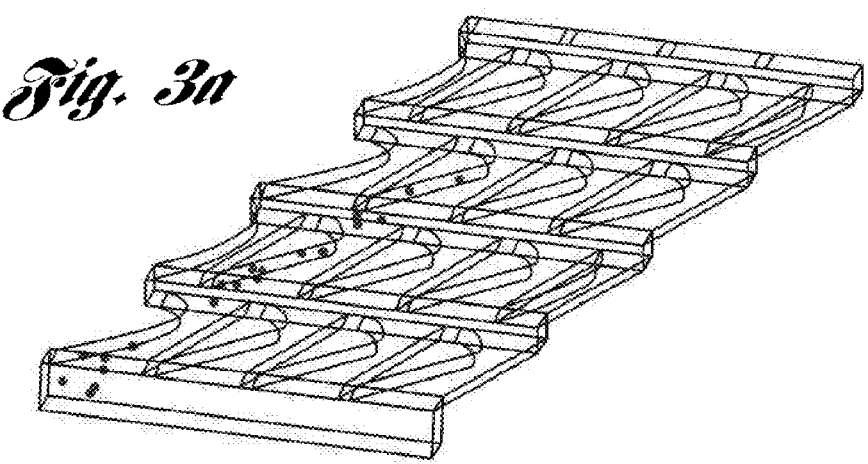
*Fig. 3a*
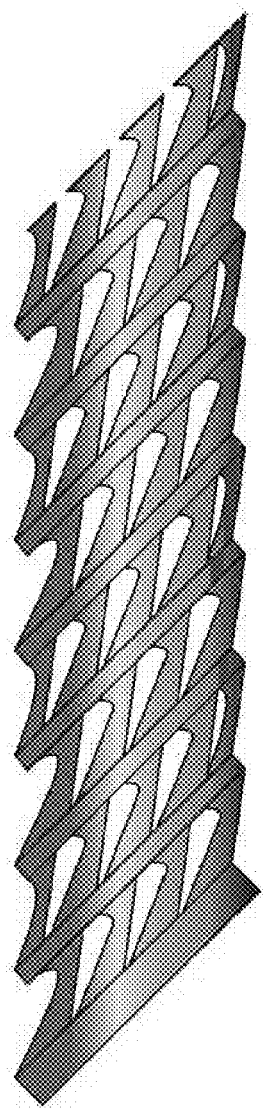 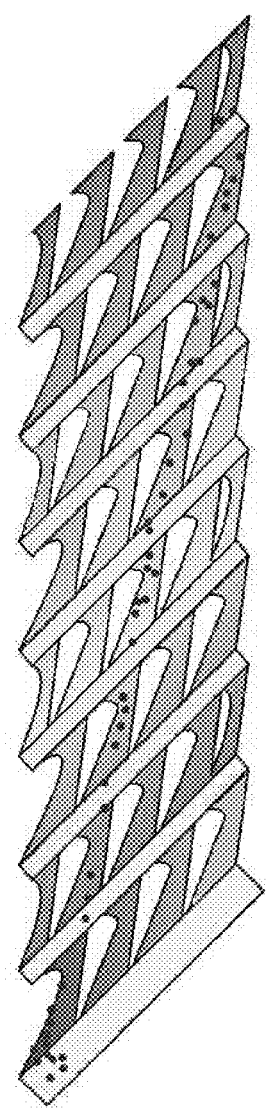
*Fig. 3b*      *Fig. 3c*

DEVICE FOR SEPARATING AND CONCENTRATING MICROFLUIDIC PARTICLES

CROSS-REFERENCE TO RELATED APPLICATIONS

This application is a continuation of International Application No. PCT/US2007/011060, filed on May 7, 2007, entitled "DEVICE AND METHOD OF SEPARATING AND CONCENTRATING MICROFLUIDIC PARTICLES" and claims the benefit of U.S. Provisional Application Ser. No. 60/797,998, filed on May 5, 2006, entitled "DEVICE AND METHOD OF SEPARATING AND CONCENTRATING MICROFLUIDIC PARTICLES," the entire contents of which are incorporated herein by reference.

BACKGROUND OF THE INVENTION

The present invention relates to flow separating and concentrating devices and, more particularly, flow units and methods of separating and concentrating microfluidic particles.

Separation of cells, bacteria, or other particles is a process typically performed in biological, medical, and chemical research. Many technologies have been developed to replace conventional gradient methods that require bulky centrifuges and separation tubes. Many of such methods and apparatus are not practical for implementation in a miniaturized or microsized and automated system. For example, field-flow fractionation (FFF) involves a flexible elution technique of simultaneous separation and measurement. Such technique requires outer fields such as gravitational fields, electrical fields, thermal gradients, or cross flow fields.

Although other techniques may not require outer fields mentioned above, many of these techniques are not continuous and require a relatively long separation time and relatively complex injecting devices. For example, capillary hydrodynamic fraction (CHDF) is a technique that was used to analyze the size distribution of particle growth during emulsion polymerization. Moreover, hydrodynamic chromatography (HDC) is a technique that has been tested on separation of fluorescent nano-spheres and macromolecules. Although both CHDF and HDC do not require external fields, these separation processes are (as mentioned) not continuous and require a relatively long separation time and complicated injecting devices. These attributes are not suitable for large-scale cell or particle preparation.

Furthermore, a preparative scale separation technique, pinched inlet split-flow thin fractionation (SPLITT) may be applied for the continuous size sorting of airborne particles. However, it requires external fields (e.g., gravitation fields) as in the case with FFF.

BRIEF SUMMARY OF THE INVENTION

The present invention generally provides microfluidic devices and methods for particle concentration and separation. Embodiments of the present invention provide continuous processing ability independent of a requirement of external fields. The devices and methods of the present invention are able to separate and concentrate particles by particle size and density. For example, the present invention provides a microfluidic separator that employs a momentum-driven particle separation principle. The separator provides a relatively high throughput with continuous-flow processing without a need of external fields for separation. The separator is configured to be stacked with arrays of other separators for large-volume cell separation. The separator has a relatively small size that is suitable as a portable device and for micro-scale analysis. Moreover, the separator is relatively cost effective and easy to be fabricated.

In one embodiment, the present invention provides a flow unit for microfluidic particle separation and concentration. The unit comprises a nozzle segment defined by a first member and a second member. The nozzle segment has an opening through which fluid and microfluidic particles enter the flow unit. The nozzle segment has a narrowing portion at which the first and second members narrow from the opening to increase momentum of the fluid through the nozzle segment. The unit further comprises a turn segment defined by the first member formed to flare outwardly downstream from the narrowing portion to change flow direction of the fluid consistent with the first member. The unit further comprises a diffuser segment defined by the second member extending past the turn segment to facilitate separation of the microfluidic particles from the fluid due to the inability to follow the fluid flow.

In another embodiment, the present invention provides a flow device for microfluidic particle separation and concentration. The device comprises a plurality of the flow units for microfluidic particle separation and concentration. The flow units are disposed in an array and are arranged in a cascading fashion.

In another example, the present invention provides a method of separating and concentrating microfluidic particles. The method comprises receiving a fluid and microfluidic particles to be separated and concentrated, and accelerating the speed of the fluid and microfluidic particles to increase the momentum thereof. The method further includes influencing a change in direction of the fluid, and facilitating separation of the microfluidic particles from the fluid due to the inability to follow the fluid flow.

Further objects, features, and advantages of the present invention will become apparent from consideration of the following description and the appended claims when taken in connection with the accompanying drawings.

BRIEF DESCRIPTION OF THE DRAWINGS

FIG. 3a is a perspective view of an array of the flow units depicting three-dimensional particle motion therethrough;

FIG. 3b is a perspective view of another array of the flow units depicting stream function of particle motion therethrough;

FIG. 3c is a perspective view of yet another array of the flow units depicting pressure and velocity distribution of particle motion therethrough;

DETAILED DESCRIPTION OF THE INVENTION

The present invention generally provides microfluidic devices and methods for particle concentration and separation. Embodiments of the present invention provide microfluidic devices having a continuous processing ability independent of a requirement for the use of external fields. The devices and methods of the present invention are able to separate and concentrate particles by particle size and density. For example, the present invention provides a microfluidic separating and concentrating device comprising a nozzle segment through which fluid and microfluidic particles enter and gain momentum, a turn segment that changes flow direction of the fluid, and a diffuser segment that facilitates separation of the microfluidic particles from the fluid.

Figure 1A:
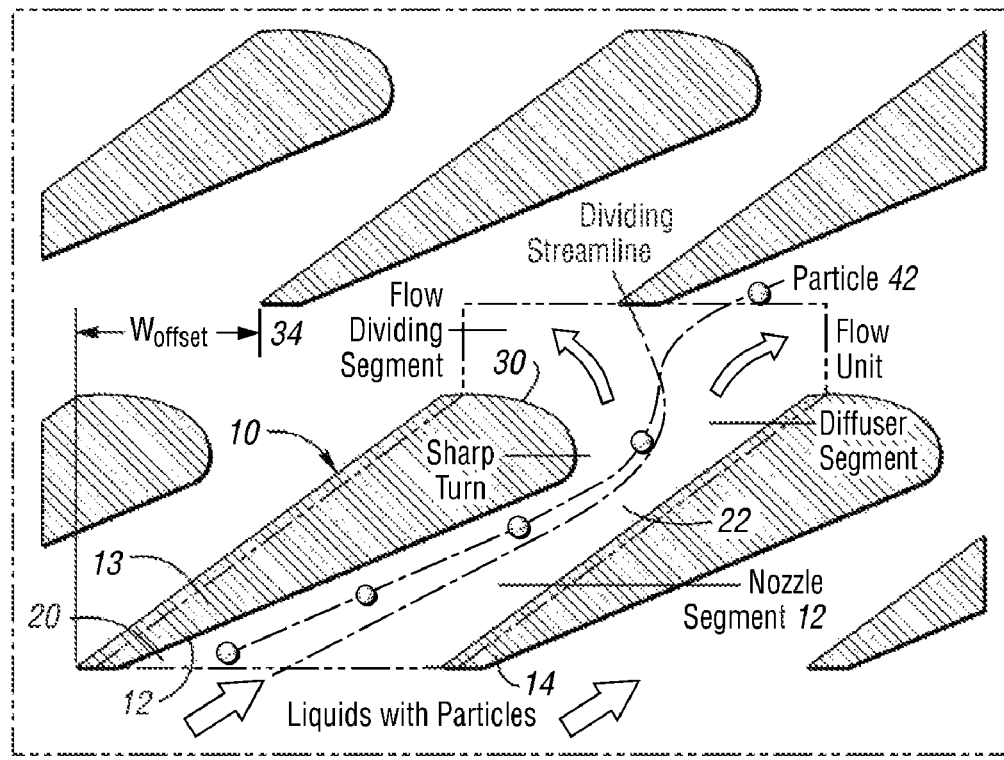
FIG. 1a is a plan view of a flow unit design for separation and concentration of microfluidic particles in accordance with one embodiment of the present invention.
Figure 1B:
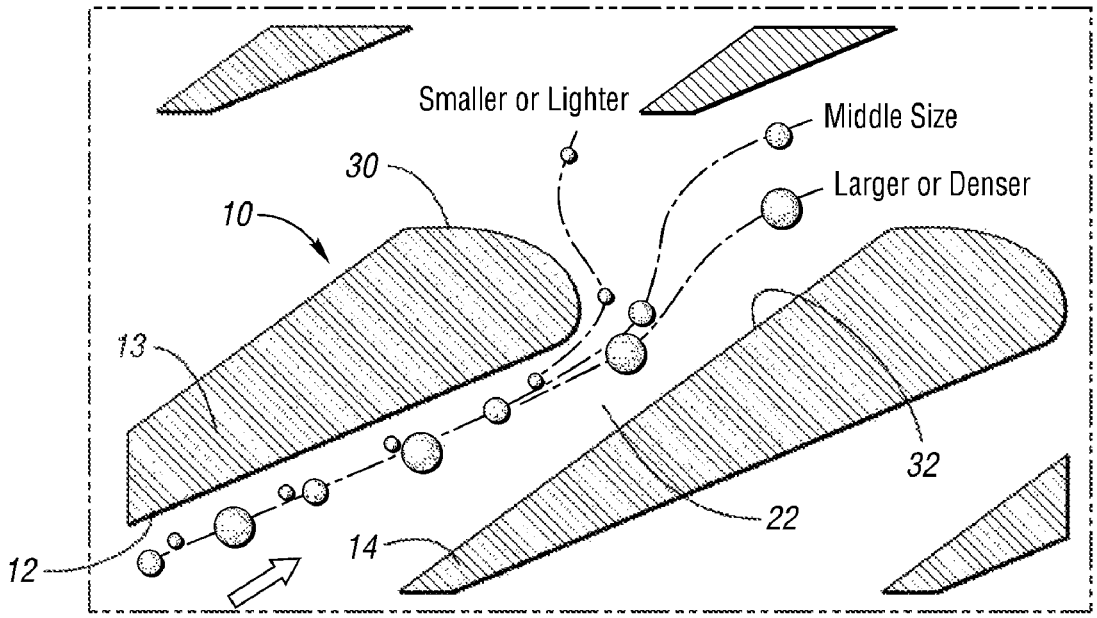
FIG. 1b is a plan view of the flow unit design in FIG. 1a depicting flow particle separation.

FIGS. 1a and 1b illustrate a flow unit 10 for microfluidic particle separation and concentration in accordance with one embodiment of the present invention. As shown, the flow unit 10 comprises a nozzle segment 12 defined by a first member 13 and a second member 14. The nozzle segment 12 has an opening 20 formed by the first and second members 13, 14 through which fluid and microfluidic particles enter the flow unit 10. Downstream from the opening 20, the nozzle segment 12 has a narrowing portion 22 at which the first and second members 13, 14 narrow relative to the opening 20. The narrowing portion 22 serves to increase momentum of the fluid and particles through the nozzle segment 12. The nozzle segment 12 accelerates the speed of fluid and particles. As result of increased momentum, particles start to resist a directional change, e.g., a change in direction near a sharp turn (discussed below).

Fluids and particles mentioned in the present application may include any suitable fluid and particle to be separated and concentrated without falling beyond the scope or spirit of the present invention. Such fluids and particles may include water and particulates thereof for applications such as bacteria detection or quality monitoring; blood components such as white and red blood cells, platelets, and plasma; target cells for applications such as isolation for disease diagnostic and genomic applications; polymer beads, ceramics, and pharmaceutical emulsions for applications such as particle sizing.

The flow unit 10 further comprises a turn segment 24 having a sharp turn 30 where, after acceleration in the nozzle segment 12, the fluid and relatively large or denser particles start to separate from each other due to the inability to follow the fluid flow. As shown, the turn segment 24 is defined by the first member 13 and is formed to flare outwardly downstream from the narrowing portion 22 to change flow direction of the fluid consistent with the first member 13. In this embodiment, the turn segment 30 is a U-shaped turn, but may be formed in any other suitable shape without falling beyond the scope or spirit of the present invention.

The increased momentum in the nozzle segment 12 forms an inability of the particles to follow the fluid flow through the directional change of the turn segment 24. Due to this inability, the particles flowing adjacent the first member 13 of the flow unit 10 are not able to follow the fluid, and other smaller or lower density particles, around the turn segment 24. Rather, the relatively larger or denser particles pass the turn segment 24 and cross the dividing streamline toward the second member 14 as shown in FIGS. 1a and 1b. Denser and larger particles have higher momentum relative to less dense and smaller particles at a constant speed, and are easier to be separated. Thus, as the average particle size or particle density decreases, the fluid drag force has a greater affect on the particle separation.

FIGS. 1a and 1b further depict a diffuser segment 32 of the flow unit 10. As shown, the diffuser segment 32 is defined by the second member 14 extending past the turn segment 24 to facilitate separation of the microfluidic particles from the fluid. The diffuser segment 32 serves to further aid in the separation at a flowing dividing segment 34 (discussed below) as shown in the particle path in FIG. 1b.

The flow unit 10 further comprises a flow dividing segment 34 where fluid flow is evenly distributed into two different openings of the two succeeding flow units. As shown in FIGS. 1a and 1b, the left side of the flow dividing segment 34 includes relatively smaller particle size and particle density than the particles that flow through the right side.

One aspect of the present invention includes a microfluidic particle separator and concentrator device having an array of the flow unit discussed above and illustrated in-part in FIGS. 1a and 1b. Such a device preferably includes a plurality of the flow unit 10 in staggering and cascading relationship. By the staggering and cascading configuration of the flow units, concentrated fluid and particles are acquired. As further shown, each stage of each flow unit has an offset, $W_{offset}$, to its preceding one. By staggering the flow units with the offset $W_{offset}$, fluids and particles may be divided into at least two downstream flow units as shown in FIG. 1a. This may also be facilitated also by splitting the exit or downstream outlet. In one embodiment, the separation of particle sizes may range between about 5 and 20 micron and particles densities ranging between about 600 and 2700 kg/m$^3$.

Flow dynamics of the microfluidic concentrator and separator device may be provided by simulation for analysis. This may be accomplished by any suitable system and software such as CFD-ACE+™ software from ESI US R&D, Inc. of Huntsville, Ala., USA.

In this example, simulation and analysis were performed. The simulation employed transient incompressible flow and spray models. The spray model was configured to track a discrete phase (e.g. solid particles) through a calculation domain by solving the governing mass, momentum, and energy conservation equations in a Lagrangian frame of reference. The flow model solved the time dependent continuity equation, the pressure-based Navier-Stokes equations, and the energy balance equation. The particles (discrete phase) can exchange momentum with the surrounding ambient fluid (continuous phase). The governing equation for the particle may be represent as follows:

$$\rho_P V_P \frac{d\vec{U}_P}{dt} = C_D \rho_L (\vec{U}_L - \vec{U}_P)|\vec{U}_L - \vec{U}_P|\frac{A_P}{2} + \rho_P V_P \vec{G} + S, \quad (1)$$

where $\rho_p$, $V_p$, and $U_p$ are the density, volume and velocity of the particle, respectively. $C_D$ is the drag coefficient of particle. $\rho_L$ and $U_L$ are the density and velocity of the surrounding liquid. $A_p$ is the particle projected area. For a spherical particle, $V_p = \pi d_P^3/6$ and $A_P = \pi d_P^2/4$ where $d_P$ is the particle diameter. G is the vector describing the acceleration of a particle due to a gravitational field and S is the additional source term. In incompressible flow, $C_D$ is a function of Reynolds number, $Re = \rho_L |U_L - U_P| d_P/\mu$, and can be evaluated as follows:

$$C_D = \frac{24}{Re} \quad \text{for} \quad Re < 1 \qquad (2)$$

$$C_D = \frac{24}{Re}(1 + 0.15Re^{0.687}) \quad \text{for} \quad 1 < Re < 10^3$$

$$C_D = 0.44 \quad \text{for} \quad Re > 10^3.$$

Figure 2:
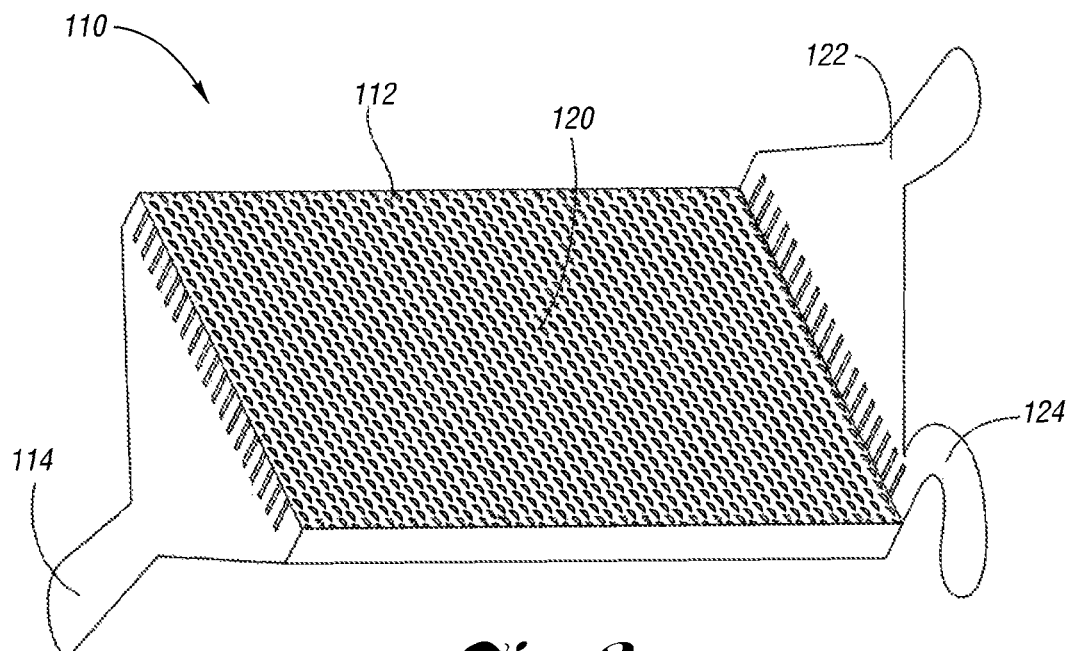
FIG. 2 is a plan view of a particle concentrator having an array of the flow units in accordance with another embodiment of the present invention.

FIG. 2 illustrates a microfluidic particle concentrator device 110 in accordance with another embodiment of the present invention. As shown, the device 110 includes an array of 25×50 flow units 112. In this embodiment, each flow unit 112 has the same components as the flow unit 10 discussed above. The device 110 comprises a sample inlet 114 through which liquids with particles may be introduced. A body 120 of the device 110 containing the array of 25×50 flow units 112 receives the liquids with particles for particle concentration. In this embodiment, fluid is split into two outlets 122,124 downstream of the flow unit array. As shown, the device comprises a liquid outlet 122 and a particle outlet 124 downstream from the body 120. Most of the liquids without or with fewer particles will exit at the liquid outlet 122. The concentrated liquids with particles may be collected at the particle outlet 124.

FIG. 3a depicts a 4×4 array of the flow units 10 (mentioned above shown in FIGS. 1a and 1b) to illustrate three-dimensional particle motion therethrough. In this embodiment, 10 μm particles were introduced into an opening of a flow unit at the far left side of the array as depicted in FIG. 3a. FIG. 3b shows (in color) a 4×8 array of the flow units to illustrate the stream function map of particle motion through the array. As it can be seen, there is a dividing streamline and divided flow as mentioned above. Moreover, velocity (vectors) and pressure (color) distribution are shown in FIG. 3c. As shown, the particles that were introduced into the opening of the flow unit at the far left side (relative to FIG. 3c) of the inlet streamlined an exit to the far right side of the outlet of the array in FIG. 3c. This shows the concentration of particles may be accomplished from any location of the inlet to one side of the outlet in a microfluidic particle concentrator comprising a 4×8 array of flow units mentioned above.

Figure 5A:
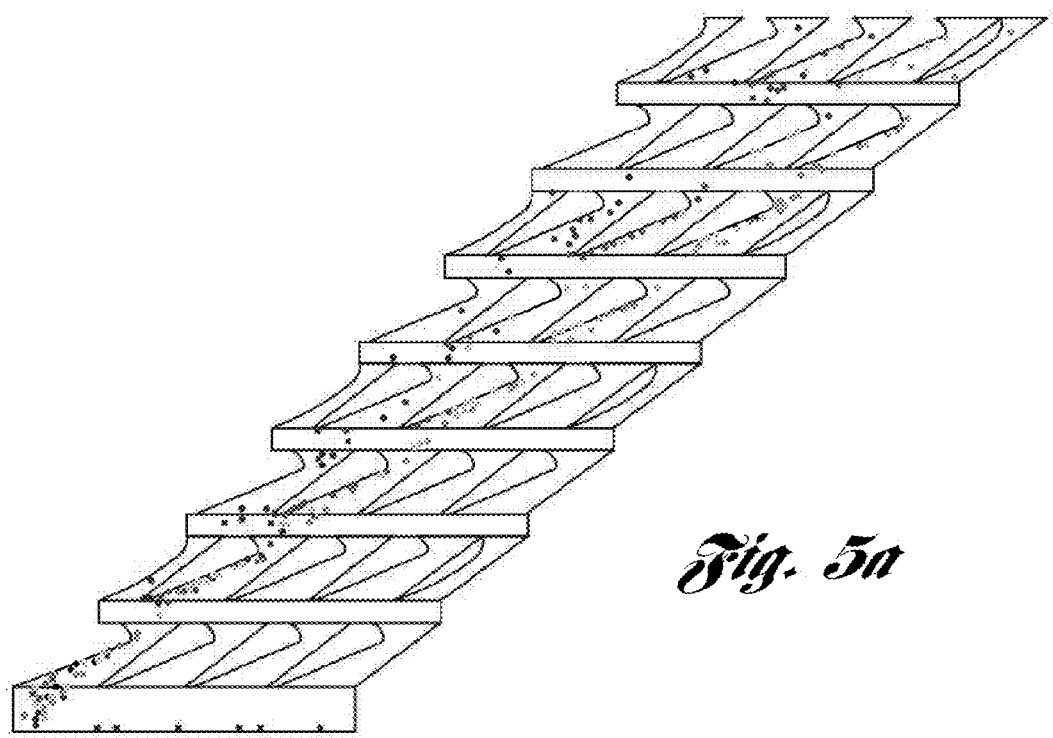
FIG. 5a is a perspective view of an array of the flow units depicting separation of particles by size.
Figure 5B:
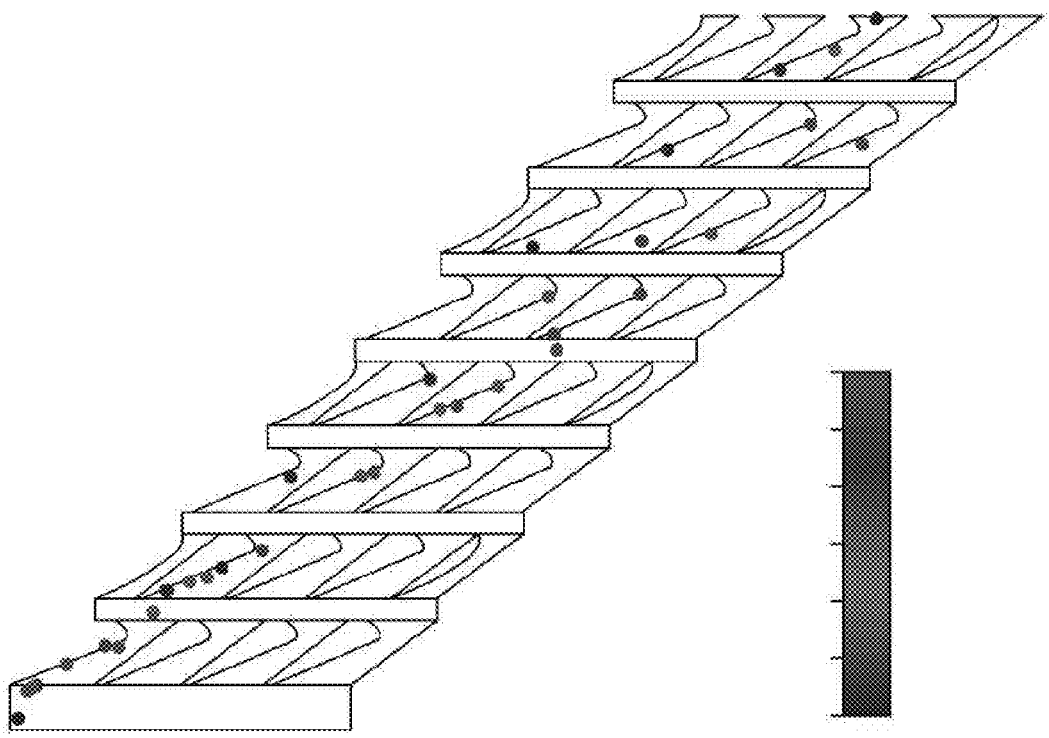
FIG. 5b is a perspective view of an array of the flow units depicting separation of particles by density.

As the fluid flows through the nozzle segment to the turn segment, the liquid experiences a centrifugal force, since its inertia tends to pull it away from the curved path of the turn segment. A pressure gradient forms and balances the force. The particles experience the same centrifugal force at the turn segment. However, since the particles have a different density than the liquid, there is a net force that pushes the particles away from the streamline of liquid. Embodiments of this microfluidic separator and connecting device employ this phenomenon to separate different particles with different densities as illustrated in FIGS. 5a and 5b.

On the other hand, as the average particle size decreases, the fluid drag force becomes more significant and suppresses the particle separation driven by the momentum. The hydrodynamics drag force depends on the particle front projected area and inertia force depends on volume (mass) of the particle. Therefore, particle separation may be performed on particles having the same density but different sizes as illustrated in FIG. 1b.

Figure 4:
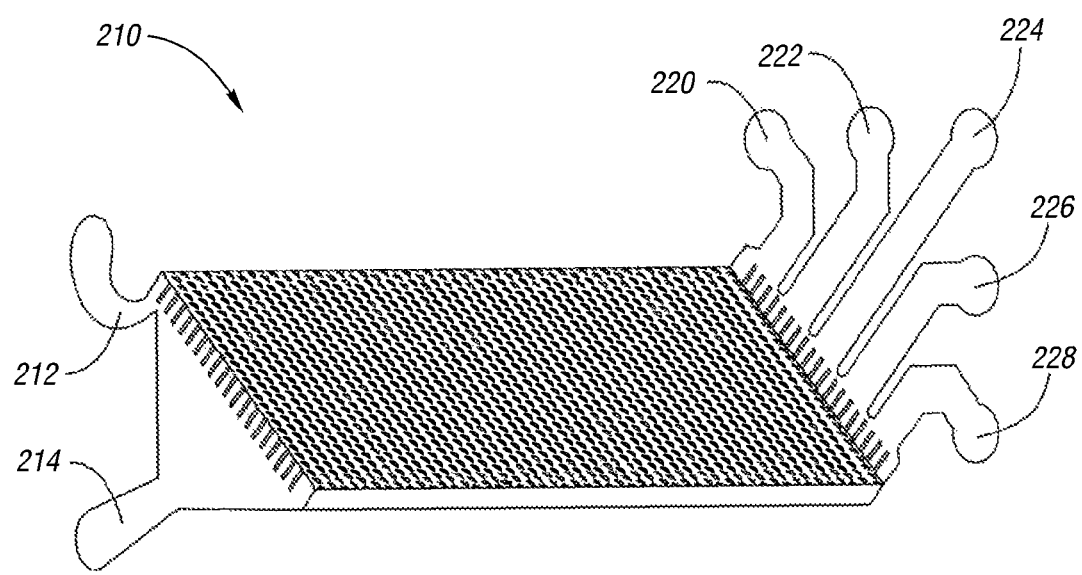
FIG. 4 is a plan view of a particle concentrator having an array of the flow units in accordance with another embodiment of the present invention.

FIG. 4 shows a design of a microfluidic particle separator device 210 with a 25×50 flow unit array (incorporating the flow units depicted in FIGS. 1a and 1b) in accordance with another embodiment of the present invention. In this embodiment, liquid with particles are introduced into an inlet portion 212 (top-left relative to FIG. 4) having a relatively small opening. Liquids without particles were fed to the relatively wider buffer inlet 214 with higher flow rate.

As shown in FIG. 4, separated particles may be collected at various ports or branches 220, 222, 224, 226, 228 at the end of the flow unit array. In this embodiment, less dense and smaller particles may collected at branch 220 while greater densities and particle sizes particles may be collected in sequence at branches 222, 224, 226, and 228.

FIGS. 5a and 5b further illustrate size and density separation by microfluidic simulation. FIG. 5a shows particle with sizes ranging from 5 to 20 μm separated. FIG. 5b shows 20 μm particles with densities ranging from 600 to 2700 Kg/m³ separated.

It is to be noted that the efficiency of particle separation may be limited when the size becomes very small, e.g., diameters less than about 1 μm. As briefly mentioned above, the limitation may be experience because the drag force is believed to be more dominant than the momentum force for the size of particles. Meanwhile, the maximum size of particles is limited by the minimum channel width of the designed device. With a relatively large array (about 100×200 or higher), a 100 times of concentration increase or more distinct particle separation may be attained with this particle separation technology.

Figure 6A:
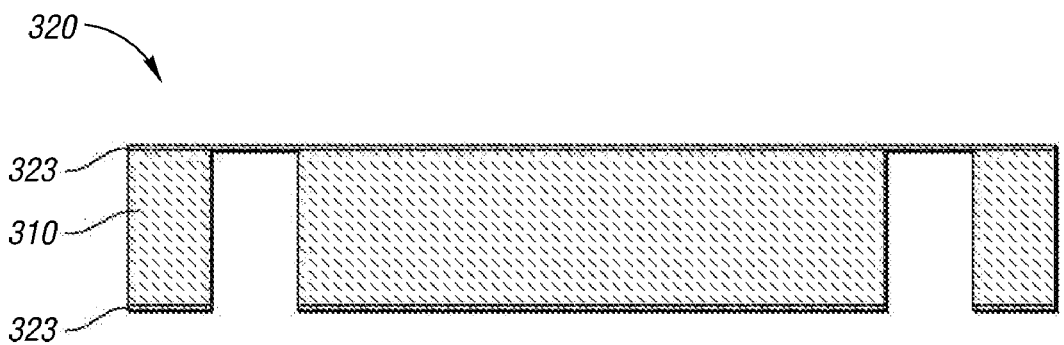
FIGS. 6a-6c are cross-sectional views of layers for fabrication of a particle concentrator in accordance with one example of the present invention.
Figure 6B:
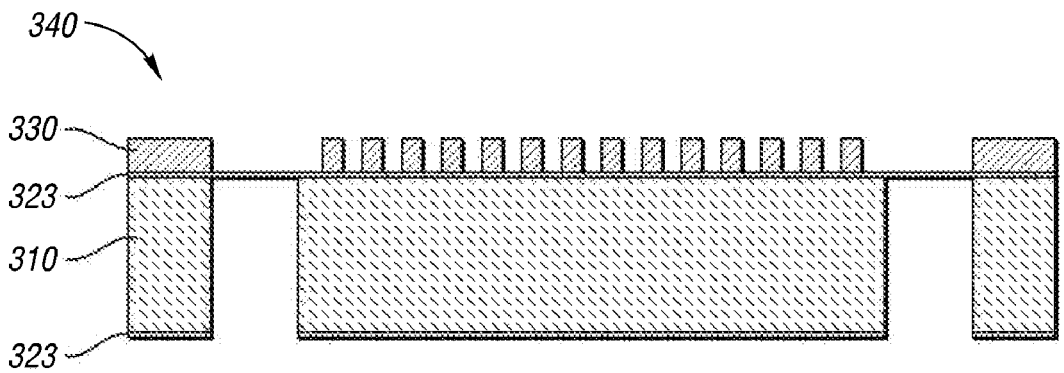
Figure 6C:
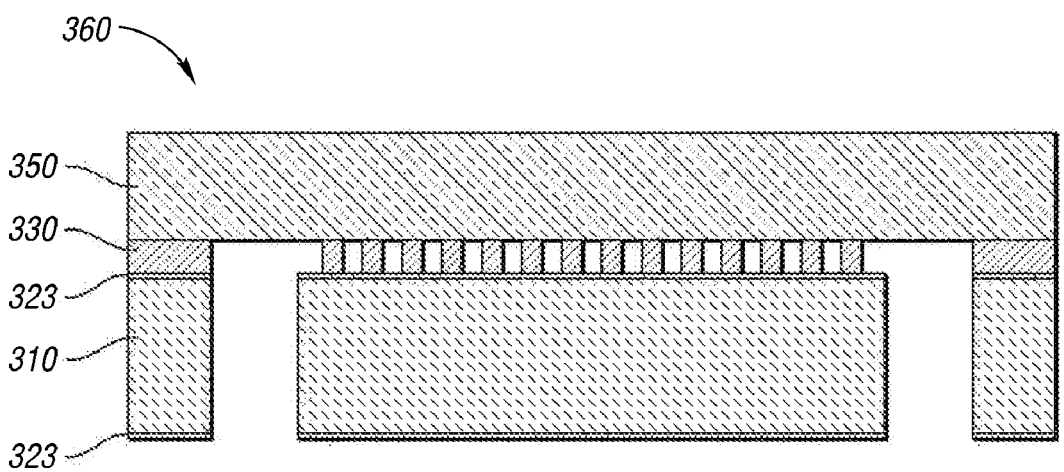

FIGS. 6a-6c depict layers or wafers for fabrication of a microfluidic particle separator and concentrator device in accordance with one example of the present invention. In this example, the layers are provided in steps in accordance with the making of an E-coli pre-concentrator. In FIG. 6a, a silicon wafer 310 is patterned using standard photolithography and is dry-etched by deep reactive ion etching to form a connection port (mask 1) 320 having oxide layers 323. In FIG. 6b, a negative photoresist SU-8 layer 330 may be used to construct the micro-sharp turn array of the mask 2 identified by reference numeral 340. SU-8 is a commonly used photoresist material, and is known to be relatively stable and inert. It is also known to provide dependable biocompatibility. In FIG. 6c, a glass (e.g., Pyrex™) wafer 350 is then used as a top cover of pre-concentrator 360 to provide optical access of a light source and a photo detector.

Further description of the present invention may be found in Appendix A, "Simulation of a Microfluidic Particle Concentrator and Separator," C.-C. Chen and G. W. Auner and Appendix B, "Mircofluidic Particle Concentrator and Separator," C.-C. Chen and G. W. Auner, of U.S. Provisional Application Ser. No. 60/797,998, filed on May 5, 2006, entitled "DEVICE AND METHOD OF SEPARATING AND CONCENTRATING MICROFLUIDIC PARTICLES," the entire contents of which are incorporated herein by reference.

While the present invention has been described in terms of preferred embodiments, it will be understood, of course, that the invention is not limited thereto since modifications may be made to those skilled in the art, particularly in light of the foregoing teachings.

The invention claimed is:

1. A flow unit for microfluidic particle separation and concentration, the unit comprising:
    a first member and a second member wherein each of the members is in the form of a wedge, each of said wedges comprising
        a first corner which flares outwardly to define a turn segment;
        a second corner at which point the wedge is more narrow than at the first corner; and
        a flat edge acting as a diffuser segment;
        wherein the first and second members are arranged such that a channel is formed;
    wherein the channel is laid out such that each of the members' second corners define a nozzle segment having an opening through which fluid and microfluidic particles enter the flow unit, and such that downstream of the nozzle segment the channel defines a narrowing portion at which the distance between the first and second members narrows from the opening to increase momentum of the fluid through the nozzle segment;

wherein the edge which defines the diffuser segment of the second member extends past the corner which defines the turn segment of the first member along an axis defined by the flow through the channel; and wherein the turn segment defined by the first corner of the first member changes the flow direction of the fluid consistent with the first member causing a separation based on the relative size of particles contained within the fluid.

2. The unit of claim 1 further comprising a flow dividing segment through which fluid flow is divided into at least two flow sides, one side of which the flow dividing segment carries relatively smaller particle size and particle density than the particles that flow through the other side.

3. The flow unit of claim 1 wherein the turn segment is a U shaped turn.

4. The unit of claim 1 wherein the first and second members are identical members.

5. The unit of claim 1 wherein the momentum and flow direction of the fluid through the flow unit is modeled as follows:

$$\rho_P V_P \frac{d\overline{U}_P}{dt} = C_D \rho_L (\overline{U}_L - \overline{U}_P)|\overline{U}_L - \overline{U}_P|\frac{A_P}{2} + \rho_P V_P \vec{G} + S.$$

wherein $\rho_p$, $V_p$, and $U_p$ are the density, volume, and velocity of the particle, respectively, wherein $C_D$ is the drag coefficient of particle, wherein $\rho_L$ and $U_L$ are the density and velocity of surrounding liquid, wherein $A_p$ is the particle projected area, wherein a spherical particle, $V_p$, is $\pi d_P^3/6$ and $A_P$ is $\pi d_P^2/4$, wherein $d_P$ is the particle diameter, and wherein G is the vector describing the acceleration of a particle due to a gravitational field and S is additional source term.

6. The unit of claim 5 wherein the fluid may be evaluated in incompressible flow as follows:

$$C_D = \frac{24}{Re} \quad \text{for} \quad Re < 1$$

$$C_D = \frac{24}{Re}(1 + 0.15Re^{0.687}) \quad \text{for} \quad 1 < Re < 10^3$$

$$C_D = 0.44 \quad \text{for} \quad Re > 10^3$$

wherein $C_D$ is a function of Reynolds number Re and wherein Re equals $\rho_L |U_L - U_P| d_p/\mu$.

7. A flow unit for microfluidic particle separation and concentration, the unit comprising:
a plurality of flow units for microfluidic particle separation and concentration, each unit comprising:
a first member and a second member wherein each of the members is in the form of a wedge, each of said wedges comprising
a first corner which flares outwardly to define a turn segment;
a second corner at which point the wedge is more narrow than at the first corner; and
a flat edge acting as a diffuser segment;

wherein the first and second members are arranged such that a channel is formed;

wherein the channel is laid out such that each of the members' second corners define a nozzle segment having an opening through which fluid and microfluidic particles enter the flow unit, and such that downstream of the nozzle segment the channel defines a narrowing portion at which the distance between the first and second members narrows from the opening to increase momentum of the fluid through the nozzle segment;

wherein the edge which defines the diffuser segment of the second member extends past the corner which defines the turn segment of the first member along an axis defined by the flow through the channel; and wherein the turn segment defined by the first corner of the first member changes the flow direction of the fluid consistent with the first member causing a separation based on the relative size of particles contained within the fluid, the flow units being disposed in an array and arranged in a cascading fashion.

8. The device of claim 7 further comprising a flow dividing segment defined by staggering each flow unit with offset.

9. The device of claim 8 wherein the flow dividing segment receives fluid flow that is divided into at least two flow sides, one side of which the flow dividing segment carries relatively smaller particle size and particle density than the particles that flow through the other side.

10. The device of claim 7 wherein the turn segment is a U-shaped turn.

11. The device of claim 7 wherein the first and second members are identical members.

12. The device of claim 7 wherein the momentum and flow direction of the fluid through the flow unit is modeled as follows:

$$\rho_P V_P \frac{d\overline{U}_P}{dt} = C_D \rho_L (\overline{U}_L - \overline{U}_P)|\overline{U}_L - \overline{U}_P|\frac{A_P}{2} + \rho_P V_P \vec{G} + S.$$

wherein $\rho_p$, $V_p$, and $U_p$ are the density, volume, and velocity of the particle, respectively, wherein $C_D$ is the drag coefficient of particle, wherein $\rho_L$ and $U_L$ are the density and velocity of surrounding liquid, wherein $A_p$ is the particle projected area, wherein a spherical particle, $V_p$, is $\pi d_P^3/6$ and $A_P$ is $\pi d_P^2/4$, wherein $d_P$ is the particle diameter, and wherein G is the vector describing the acceleration of a particle due to a gravitational field and S is additional source term.

13. The device of claim 5 wherein the fluid may be evaluated in incompressible flow as follows:

$$C_D = \frac{24}{Re} \quad \text{for} \quad Re < 1$$

$$C_D = \frac{24}{Re}(1 + 0.15Re^{0.687}) \quad \text{for} \quad 1 < Re < 10^3$$

$$C_D = 0.44 \quad \text{for} \quad Re > 10^3$$

wherein $C_D$ is a function of Reynolds number Re and wherein Re equals $\rho_L |U_L - U_P| d_p/\mu$.

* * * * *